(12) United States Patent
Ma et al.

(10) Patent No.: US 11,564,962 B2
(45) Date of Patent: Jan. 31, 2023

(54) PHARMACEUTICAL COMPOSITION COMPRISING MAPLE LEAF EXTRACT FOR PREVENTING OR TREATING RETINAL DISEASE

(71) Applicant: KOREA INSTITUTE OF ORIENTAL MEDICINE, Daejeon (KR)

(72) Inventors: Jin Yeul Ma, Daejeon (KR); Kwang Il Park, Daegu (KR); Yeoun-Hee Kim, Daegu (KR); Tae Woo Oh, Daegu (KR); Won Kyung Cho, Daegu (KR); Dong-Gun Kim, Daegu (KR); Eun Hee Park, Seoul (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 242 days.

(21) Appl. No.: 16/325,958

(22) PCT Filed: Aug. 11, 2017

(86) PCT No.: PCT/KR2017/008784
§ 371 (c)(1),
(2) Date: Jul. 5, 2019

(87) PCT Pub. No.: WO2010/034465
PCT Pub. Date: Feb. 22, 2018

(65) Prior Publication Data
US 2019/0328808 A1   Oct. 31, 2019

(30) Foreign Application Priority Data
Aug. 16, 2016   (KR) ........................ 10-2016-0103745

(51) Int. Cl.
*A61K 36/20* (2006.01)
*A23L 33/105* (2016.01)
*A61P 27/02* (2006.01)

(52) U.S. Cl.
CPC ............ *A61K 36/20* (2013.01); *A23L 33/105* (2016.08); *A61P 27/02* (2018.01); *A23V 2002/00* (2013.01); *A23V 2200/30* (2013.01); *A23V 2250/21* (2013.01)

(58) Field of Classification Search
None
See application file for complete search history.

(56) References Cited

FOREIGN PATENT DOCUMENTS

| | | |
|---|---|---|
| CN | 101480417 | 7/2009 |
| JP | 11318209 A * | 5/1998 |
| JP | 2008266278 | 11/2008 |
| KR | 20100004466 | 1/2010 |
| KR | 10-2012-0068432 | 6/2012 |
| KR | 10-2013-0133338 | 12/2013 |

OTHER PUBLICATIONS

American Foundation for the Blind 2021 https://www.afb.org/blindness-and-low-vision/eye-conditions#:~:text=The%20most%20common%20form%20of,dystrophy%2C%20and%20retinal%20cone%20dystrophy.&text=Any%20of%20various%20conditions%20present,affect%20the%20eyes%20or%20visionn.*
Honma, A. et al., 'Antihyperglycemic effects of Japanese maple Acer amoenum leaf extract and its constituent corilagin' Journal of Wood Science, 2010, vol. 56, pp. 507- 512.
Kim, J. H. et al., The isolation and antioxidative effects of vitexin from Acer palmatum Archives of Pharmacal Research, 2005, vol. 28, No. 2, pp. 195-202.
Wang, J. et al., 'Purified vitexin compound 1 inhibits growth and angiogenesis through activation of FOXO3a by inactivation of Akt in hepatocellular carcinoma' International Journal of Molecular Medicine, 2014, vol. 33, pp. 441-448.
Zhu, Q. et al., Antinociceptive effects of vitexin in a mouse model of postoperative pain Scientific Reports, Jan. 14, 2016, vol. 6, thesis No. 19266, internal pp. 1-10.
Siu, Andrew W., et al. "Glutamate-induced retinal lipid and protein damage: the protective effects of catechin." *Neuroscience letters* 432.3 (2008): 193-197.
Xia, "Study on Microwave Extraction and HPLC Analysis of Plant Polyphenols in Maple Leaves", dated 2009, downloaded from https://xueshu.baidu.com/usercenter/paper/show?paperid=f5e8d866864fd2dec39d82bd0df7fd7a on May 21, 2021.
Office Communication issued in corresponding Chinese Application No. 201780063585.3, dated Apr. 15, 2021.

* cited by examiner

*Primary Examiner* — Terry A McKelvey
*Assistant Examiner* — Catheryne Chen
(74) *Attorney, Agent, or Firm* — ParkerHighlander, PLLC

(57) ABSTRACT

The present invention relates to a pharmaceutical composition comprising a maple leaf extract or fraction thereof for preventing or treating a retinal disease, a method for preventing or treating a retinal disease using the pharmaceutical composition, and a food composition comprising a maple leaf extract or fraction thereof for ameliorating the symptoms of a retinal disease.

The pharmaceutical composition according to the present invention, which is effective for the treatment of a retinal disease, can be used pharmaceutically as a composition for preventing or treating a retinal disease, and can also be used advantageously as a health functional food.

3 Claims, 14 Drawing Sheets

PKCα; Rod bipolar cells

OPN1SW; outer segments of cones

PHARMACEUTICAL COMPOSITION COMPRISING MAPLE LEAF EXTRACT FOR PREVENTING OR TREATING RETINAL DISEASE

This application is a national phase application under 35 U.S.C. § 371 of International Application No. PCT/KR2017/008784, filed Aug. 11, 2017, which claims priority to Korean Application Nos. 10-2016-0103745, filed Aug. 16, 2016. The entire text of each of the above referenced disclosures is specifically incorporated herein by reference.

TECHNICAL FIELD

The present invention relates to a pharmaceutical composition for preventing or treating a retinal disease containing a maple leaf extract, and more specifically, to a pharmaceutical composition for preventing or treating a retinal disease containing a maple leaf extract or fraction thereof, a method for preventing or treating a retinal disease using the pharmaceutical composition, and a food composition for ameliorating the symptoms of a retinal disease containing a maple leaf extract or fraction thereof.

BACKGROUND ART

Maple trees grow to a height of around 100 m, have small, bare branches, and have a reddish brown color. Additionally, maple leaves are opposite and palmately lobed with 5 to 7 deeply divided lobes. The divided lobes are of a wide lanceolate shape with sharp ends and biserrate edges and are 5 cm to 6 cm long. Their petioles are red and 3 cm to 5 cm long. The staminate flowers and bisexual flowers bloom on the same tree. Maple flowers with a dark red color bloom in May and the flowers run in corymbs at the ends of the branches. Each flower has five sepals with soft hairs, five petals, and eight stamens.

The rhizodermis and branches of these maple trees are used as herbal medicine, being boiled down and taken for severe pain due to knee arthritis, and it is used for bone fracture by mixing with *Acanthopanax* (also called "thorny ginseng"), and is known to have anti-inflammatory and detoxifying effects.

Meanwhile, the retina is transparent nerve tissue that covers the innermost part of the eyeball, and the light entering the eyeball passes through the inner layer of the retina and is detected by the visual cells of the retina. The visual cells convert light information back into electrical information, which passes through the optic nerve via the cells of the inner layer of the retina and is transmitted to the brain. The retina consists of ten layers from the outside to the inside of the eyeball. The ten constituent layers correspond to the retinal pigment epithelium layer, the photoreceptor layer, the outer boundary membrane, the outer nuclear layer, the outer plexiform layer, the inner nuclear layer, the inner plexiform layer, the ganglion cell layer, the nerve fiber layer, and the inner boundary layer. Additionally, the macula is an elliptical depression present in a slightly outer lower part of the optic disc, and is a region where the optic nerve cells of the retina are densely aggregated. Most functions of recognizing visual stimuli in the retina are performed at the macula, and therefore, in cases where a lesion occurs in the macula, or damage or defects occur in the optic nerve cells of the macula, the result may be blindness or severe visual impairment.

All diseases caused by loss of the retina or macula are included under retinal disease (or retinal disorder). Specific examples of retinal diseases are as follows.

Among the retinal diseases, examples of diseases belonging to retinal circulatory disorder include retinal artery occlusion, retinal vein occlusion, retinal periphlebitis, hypertensive retinopathy, diabetic retinopathy, retinopathy of prematurity, etc.

Additionally, representative retinitis may include sensory neuroretinal inflammation due to bacteria or fungi, inflammation of the retinal pigment epithelium identified in newborns born to rubella-infected mothers, etc., and these diseases also belong to the retinal diseases caused by retinal damage.

Additionally, diseases that cause retinal degeneration may include retinitis pigmentosa, angioid streaks, drusen, etc., and these diseases also belong to the retinal diseases caused by retinal damage.

Additionally, retinal detachment occurs as the distance increases between the inner sensory nerve layer of the retina and the outer layer of the retinal pigment epithelium. Retinal detachment is largely divided into rhegmatogenous retinal detachment and non-rhegmatogenous retinal detachment depending on whether or not it is caused by retinal tear, and these diseases also belong to the retinal diseases caused by retinal damage.

Other retinal diseases may include macular degeneration, macular dystrophy, diabetic retinopathy, retinal arteriovenous occlusion, hypertensive retinopathy, retinal aortic aneurysm, retinal ischemic syndrome, radiation retinopathy, retinopathy of prematurity, acute retinal necrosis, retinitis, retinal choroiditis, retinal detachment, retinal tumor, retinal damage due to trauma, retinal damage due to light, etc.

Although studies on the treatment of these retinal diseases are actively underway, no complete treatment method has been reported thus far. In particular, there is a problem in that surgery is still the only treatment for retinal diseases, and to date, no technology has been reported with respect to pharmaceutical compositions or drug therapies effective in the prevention or treatment of these retinal diseases.

Meanwhile, as a prior art document related to the present invention, Korean Patent Application Publication No. 2012-0068432 (Patent Document 1) is disclosed. However, Patent Document 1 only discloses a composition for preventing and treating diabetes and obesity, containing an ethanol extract of *Aceriphyllum rossii* leaves, but it does not disclose anything on an effect of preventing or treating retinal diseases using a maple leaf extract.

DISCLOSURE

Technical Problem

The present inventors have made efforts to develop a novel material effective for the prevention or treatment of retinal diseases. As a result, they have confirmed that a pharmaceutical composition containing a maple leaf extract has the effect of preventing or treating retinal diseases, thereby completing the present invention.

Technical Solution

A primary object of the present invention is to provide a pharmaceutical composition for preventing or treating a retinal disease, containing a maple leaf extract or fraction thereof.

Another object of the present invention is to provide a method for treating a retinal disease including administering the pharmaceutical composition to a subject.

Still another object of the present invention is to provide a food composition for ameliorating the symptoms of a retinal disease, containing a maple leaf extract or fraction thereof.

Still another object of the present invention is to provide a feed composition for ameliorating the symptoms of a retinal disease, containing a maple leaf extract or fraction thereof.

Advantageous Effects of the Invention

The pharmaceutical composition according to the present invention, which is effective for the treatment of a retinal disease, can be used pharmaceutically as a composition for preventing or treating a retinal disease, and can also be used advantageously as a health functional food.

BRIEF DESCRIPTION OF DRAWINGS

FIGS. 6a-b show experimental results confirming the cell death of retinal ganglion cells after eye drop or ocular administration of a maple leaf extract according to the present invention, in which FIG. 6a shows fluorescence microscopic images and FIG. 6b shows a graph illustrating the results where the number of cells showing a positive reaction in a selected image was calculated and then converted to an average value for the control group.

FIGS. 7a-b show experimental results confirming the inhibition of a decrease in retinal ganglion cell fibers after eye drop or oral administration of a maple leaf extract according to the present invention, in which FIG. 7a shows fluorescence microscopic images and FIG. 7b shows a graph illustrating the measurement results of expression levels of nerve fibers showing a positive reaction to Tuj-1.

FIGS. 8a-b show experimental results confirming the inhibition of the activities of neuroglial cells and astrocytes after eye drop or oral administration of a maple leaf extract according to the present invention, in which FIG. 8a shows fluorescence microscopic images and FIG. 8b shows a graph illustrating the measurement results of expression levels which were significantly decreased in all groups by KIOM-2015EE.

FIGS. 9a-b show experimental results confirming the changes from the view of retinal histology after eye drop or oral administration of a maple leaf extract according to the present invention, in which FIG. 9a shows fluorescence microscopic images and FIG. 9b is a graph showing the average value for the control group after counting the number of cells remaining in the ganglion cell layer in a selected image.

BEST MODE

Figure 1:
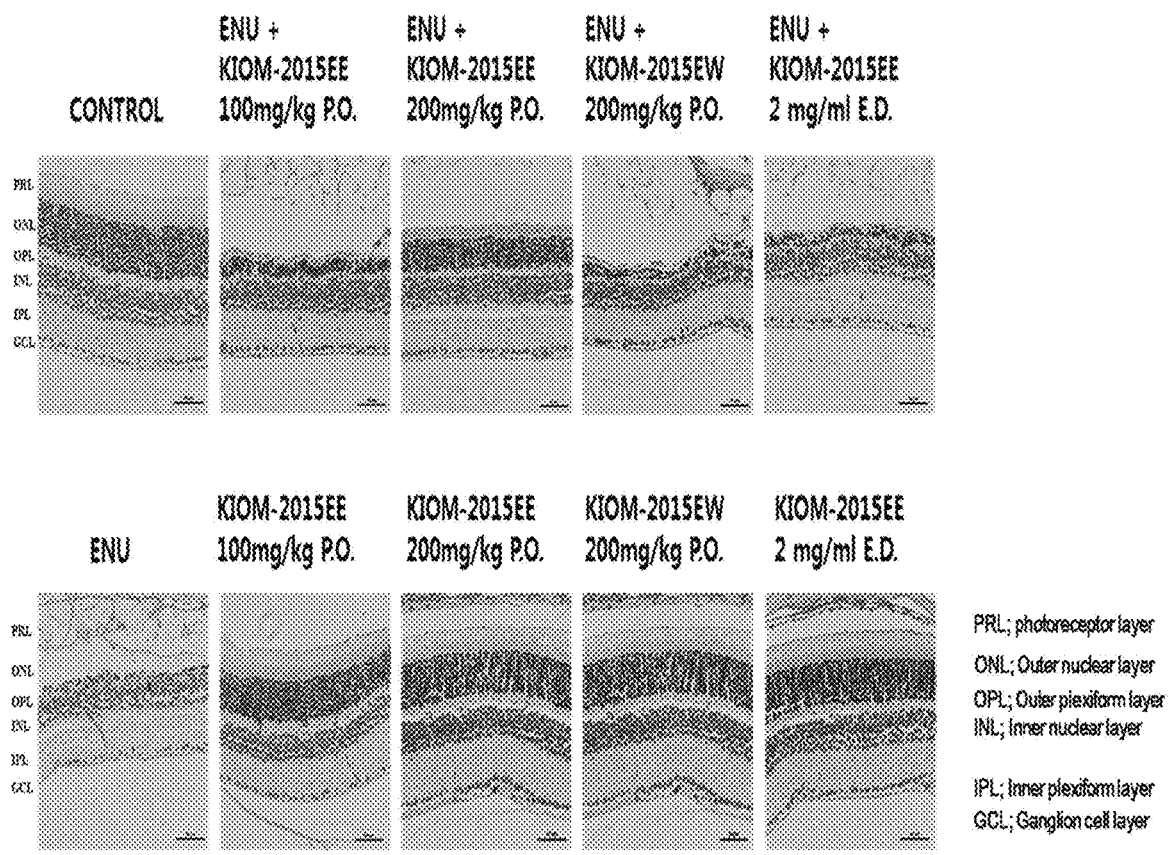
FIG. 1 shows images illustrating the results of immunohistochemical staining observed after oral or ocular administration of a maple leaf extract according to the present invention, in which a significant effect of retinal protection exhibited by the oral administration was confirmed.

The present inventors have conducted various studies to develop a preparation derived from a natural product capable of safely and effectively treating retinal diseases, and as a result, they have discovered that a maple leaf extract has an effect of treating retinal diseases. In general, maple trees are known to show various pharmacological effects. However, there have been no reports on the use of maple trees for the treatment of retinal diseases. Additionally, except for currently available invasive therapies, thus far, no technology has been reported with respect to pharmaceutical compositions and drug therapies which are effective for preventing or treating retinal diseases.

The present inventors have predicted that a maple leaf extract will be able to exhibit an effect for treating retinal diseases, and based on this assumption, the present inventors have conducted various studies to identify active ingredients that may be associated with the effect of the maple leaf extract for the treatment of retinal diseases, and as a result, they have confirmed that a maple leaf extract has an effect for treating retinal diseases. That is, the present inventors have confirmed that a maple leaf extract is able to reduce the expression of at least one selected from the group consisting of Cleaved PARP, GFAP, and Nestin while increasing the expression of at least one selected from the group consisting of OPNISW, Brn3a, and Tuj-1, thereby exhibiting an effect of treating retinal diseases.

As described above, it has not been known that a maple leaf extract exhibits an effect of treating retinal diseases, and such fact was first confirmed by the present inventors. Additionally, a pharmaceutical composition having an effect of treating retinal diseases was also first invented by the present inventors.

To achieve the above objects, an aspect of the present invention provides a pharmaceutical composition for the prevention or treatment of retinal diseases containing a maple leaf extract or fraction thereof.

Additionally, another aspect of the present invention provides a use of a maple leaf extract or fraction thereof for the prevention or treatment of retinal diseases.

Hereinafter, the pharmaceutical composition for the prevention or treatment of retinal diseases containing a maple leaf extract or fraction thereof of the present invention is described in detail.

As used herein, the term "maple tree" refers to a tree which grows to a height of around 100 m, has small, bare branches, and has a reddish brown color, and maple tree leaves are opposite and palmately lobed with 5 to 7 deeply divided lobes. Meanwhile, a maple tree be largely divided into roots, stems, and leaves, and a pharmaceutical composition of the present invention may contain a maple leaf extract or fraction thereof. In particular, according to the part of the maple tree, the extract or fraction thereof may be able to achieve the effect of preventing or treating retinal diseases without any particular limitation on the part of the maple tree.

As used herein, the term "extract" refers to one which is extracted from maple leaves using an appropriate solvent, and the extract may include, for example, all of a hot water extract, a polar solvent-soluble extract, and a non-polar solvent-soluble extract of maple leaves.

As the suitable solvent for extracting an extract from maple leaves, any solvent acceptable in the art may be used, and water or an organic solvent may be used. For example, various kinds of solvents, such as purified water, $C_{1-4}$ alcohols including methanol, ethanol, propanol, isopropanol, butanol, etc., acetone, ether, benzene, chloroform, ethyl acetate, methylene chloride, hexane, cyclohexane, etc., may be used alone or in combination, but the solvent is not limited thereto.

As the extraction method, a method selected from a hot water extraction method, cold-precipitation extraction method, reflux cooling extraction method, solvent extraction method, steam distillation method, ultrasonic extraction method, elution method, pressing method, etc. may be used. Additionally, the desired extract may further be subjected to a conventional fractionation process or may be purified using a conventional purification method. The method for preparing a maple leaf extract of the present invention is not limited, but any method known in the art may be used.

For example, the maple leaf extract to be contained in the composition of the present invention may be prepared as a powder by subjecting the primary extract extracted by the hot water extraction method or solvent extraction method via an additional process (e.g., vacuum distillation, freeze drying, spray drying, etc.). Additionally, the primary extract may be prepared into a further purified fraction using various chromatography methods (e.g., silica gel column chromatography, thin layer chromatography, high performance liquid chromatography, etc.).

Accordingly, in the present invention, a maple leaf extract is a concept that includes all of the extracts, fractions, and purified products, as well as dilutions, concentrates, or dried products thereof obtained in each step of extraction, fractionation, and purification.

The composition of the present invention containing such a maple leaf extract as an active ingredient may be a pharmaceutical composition.

As used herein, the term "fraction" refers to a resulting product obtained by performing fractionation to separate a particular component or particular component group from a mixture containing various components.

In the present invention, the fraction may be product resulting from fractionation of the maple leaf extract by various methods (e.g., a solvent fractionation method, ultrafiltration fractionation method, chromatographic fractionation method, etc.).

The method for obtaining the fraction is not particularly limited as long as a fraction exhibiting an effect of preventing or treating retinal diseases can be obtained using the method, and a conventional method used in the art may be used. In an embodiment, a method of obtaining a fraction from a hot water maple extract using a solvent fractionation method may be used.

In the present invention, the type of the fraction solvent used for obtaining the fraction is also not particularly limited, as long as a fraction exhibiting an effect of preventing or treating retinal diseases can be obtained using the solvent, and any method conventionally used in the art may be used. In an embodiment, as the fraction solvent, a polar solvent (e.g., water, alcohol, etc.), non-polar solvent (e.g., hexane, ethyl acetate, chloroform, dichloromethane, etc.), etc. may be used alone or as a mixture of at least one thereof.

As used herein, the term "retinal disease" collectively refers to diseases in which vision loss or damage occurs due to damage to the retina or macula or degeneration thereof.

Meanwhile, the pharmaceutical composition relates to the ameliorating the symptoms of a retinal disease. Specific examples of the retinal disease may include retinal artery occlusion, retinal vein occlusion, retinal periphlebitis, hypertensive retinopathy, diabetic retinopathy, retinopathy of prematurity, sensory neuroretinal inflammation, inflammation of the retinal pigment epithelium, retinitis pigmentosa, angioid streaks, drusen, rhegmatogenous retinal detachment, non-rhegmatogenous retinal detachment, macular degeneration, macular dystrophy, diabetic retinopathy, retinal arteriovenous occlusion, hypertensive retinopathy, retinal aortic aneurysm, retinal ischemic syndrome, radiation retinopathy, retinopathy of prematurity, acute retinal necrosis, retinitis, retinal choroiditis, retinal detachment, retinal tumor, retinal damage due to trauma, or retinal damage due to light.

As used herein, the term "prevention" refers to all activities that suppress or delay the onset of retinal diseases by administration of the pharmaceutical composition of the present invention, and the term "treatment" refers to all activities that improve or advantageously change the symptoms of retinal diseases by administration of the pharmaceutical composition of the present invention.

The pharmaceutical composition of the present invention for the prevention or treatment of retinal diseases, which contains a maple leaf extract or a pharmaceutically acceptable salt thereof as an active ingredient, may further include a suitable carrier (as a specific example, a non-naturally occurring carrier), excipient, disintegrant, sweetener, binder, coating agent, swelling agent, lubricant, glidant, flavoring agent, or diluent which is conventionally used for the preparation of pharmaceutical compositions.

Additionally, the maple leaf extract or fraction thereof may be used specifically in an amount of 1 to 80 parts by weight, and more specifically 20 to 60 parts by weight relative to the 100 parts by weight of the total weight of the composition, but the amount of the maple leaf extract or fraction thereof is not particularly limited thereto. When the maple leaf extract or fraction thereof is contained in an amount of less than 1 part by weight, it is difficult to sufficiently exhibit the effect for preventing or treating retinal diseases to be achieved in the present invention, and thus this may not be considered as an exemplary embodiment of the present invention. Meanwhile, when the maple leaf extract or fraction thereof is contained in an amount of greater than 80 parts by weight, it is not possible to limit the content of the remaining materials to be prepared into a product for pharmaceutical application, and thus this may not be considered as an exemplary embodiment of the present invention.

Meanwhile, the pharmaceutical composition for the prevention or treatment of retinal diseases may be specifically administered intraarterially or intravenously, subcutaneously, intrarectally, intranasally, or via any arbitrary parenteral routes, and more specifically intraarterially or intravenously, orally, or directly into muscle cells, but the administration method is not particularly limited thereto.

Additionally, the dose level selected from the composition will depend on the activity of a compound, administration route, severity of the conditions being treated, and conditions and previous medical history of the patient being treated. However, it is well within the knowledge of the art that a dose of the compound is begun at a level lower than that required for achieving the desired therapeutic effect and is gradually increased until the desired effect is achieved. The desired dose may be determined by age, sex, body type, and body weight. The composition may be further processed before being formulated into a pharmaceutically acceptable preparation, and specifically may be pulverized or polished into smaller particles. Additionally, the composition may vary depending on the conditions and the patient being treated, but this may be determined without creativity.

Additionally the pharmaceutical composition may have any one formulation type selected from the group consisting of tablets, pills, powders, granules, capsules, suspensions, internal use solutions, emulsions, syrups, sterile aqueous solutions, non-aqueous solvents, emulsions, lyophilized preparations, and suppositories, and may be prepared in various oral or parenteral formulation types. For formulation, a diluent or excipient (e.g., a filler, extender, binder, humectant, disintegrant, surfactant, etc.) is commonly used. Examples of solid preparations for oral administration may include tablets, pills, powders, granules, capsules, etc. These solid preparations are prepared by mixing one or more compounds with at least one excipient (e.g., starch, calcium carbonate, sucrose or lactose, gelatin, etc.). Additionally, in addition to simple excipients, lubricants (e.g., magnesium stearate, talc, etc.) may also be used. Liquid preparations for oral administration may include suspensions, internal use solutions, emulsions, syrups, etc., and various excipients (e.g., humectants, sweetening agents, fragrances, preservatives, etc.) may be included, in addition to the commonly used simple diluents (e.g., water and liquid paraffin). Preparations for parenteral administration may include sterile aqueous solutions, non-aqueous solutions, suspensions, emulsions, lyophilized preparations, and suppositories. Examples of the non-aqueous solutions and suspensions may include vegetable oils (e.g., propylene glycol, polyethylene glycol, and olive oil), an injectable ester (e.g., ethyl oleate), etc. Examples of the bases for the suppositories may include Witepsol, macrogol, Tween 61, cacao butter, laurinum, glycerogelatin, etc.

The composition of the present invention may be administered in a pharmaceutically effective amount.

As used herein, the term "pharmaceutically effective amount" refers to an amount sufficient for the treatment of diseases at a reasonable benefit/risk ratio applicable to medical treatment, and the level of the effective dose may be determined based on the factors including the kind of subject and severity of illness, age, sex, kind of disease, drug activity, drug sensitivity, administration time, administration route and dissolution rate, length of treatment, factors including a drug to be used simultaneously in combination, and other factors well known in the medical field. The composition of the present invention may be administered as an individual therapeutic agent, in combination with another therapeutic agent, or sequentially or simultaneously with a conventional therapeutic agent, and may be administered once or multiple times. It is important that the pharmaceutical composition be administered in the minimum amount that can obtain the maximum effect without adverse effects considering all of the factors described above, and the pharmaceutically effective amount can easily be determined by one of ordinary skill in the art. A desired dose of the composition of the present invention may vary depending on the health status and body weight of a patient, severity of disease, drug type, and administration route and duration, and an appropriate total daily dose may be determined within the scope of correct medical judgment by a practitioner. In general, the composition of the present invention may be administered once or several times in divided doses, in an amount of 0.001 mg/kg to 1,000 mg/kg, specifically 0.05 mg/kg to 500 mg/kg, and more specifically 0.1 mg/kg to 500 mg/kg. In particular, when the pharmaceutical composition of the present invention is administered in an amount of 100 mg/kg to 300 mg/kg, an excellent effect of preventing or treating retinal diseases can be achieved. The composition is not particularly limited, but any subject can be applied as long as it is a subject for the prevention or treatment of retinal diseases. For example, the composition may be applied to any subject, such as a non-human animal (e.g., monkeys, dogs, cats, rabbits, marmots, rats, mice, cattle, sheep, pigs, etc.). The administration method may include, without limitation, any conventional method in the art; for example, peritoneal administration, ocular administration, or oral administration may be used, but the administration method is not limited thereto.

Meanwhile, the pharmaceutical composition may be one which reduces the expression of at least one selected from the group consisting of Cleaved PARP, GFAP, and Nestin.

Additionally, the pharmaceutical composition may be one which increases the expression of OPN1SW, Brn3a, Tuj-1, etc.

To achieve the above objects, still another aspect of the present invention provides a method for treating retinal diseases, which includes administering the pharmaceutical composition to a subject.

In the present invention, the subject suspected of having a retinal disease refers to all animals which have or are at risk of developing a retinal disease, and the subject suspected of having a retinal disease can be effectively treated by administration of the pharmaceutical composition of the present invention.

As used herein, the term "administration" refers to the introduction of the pharmaceutical composition of the present invention to a subject suspected of having a retinal disease in an appropriate manner, and the pharmaceutical composition may be administered via various oral and parenteral routes as long as the pharmaceutical composition can reach the target tissue. Specifically, the pharmaceutical composition may be administered via peritoneal, ocular, or oral administration, but the administration route is not limited thereto.

Still another aspect of the present invention provides a food composition for ameliorating the symptoms of a retinal disease, comprising a maple leaf extract or fraction thereof.

The maple leaf extract or fraction thereof may be habitually eaten or may be prepared in the form of a food to ameliorating the symptoms of a retinal diseases. In particular, the amount of the maple leaf extract or fraction thereof contained in the food may be in an amount of 0.001 wt % to 10 wt %, and more preferably 0.1 wt % to 1 wt % relative to the total weight of a food composition, but the amount of the maple leaf extract or fraction thereof is not limited thereto. When the food is a beverage, the retinal extract or fraction thereof may be contained in an amount of 1 g to 10 g, and more preferably 2 g to 7 g, based on 100 mL of the beverage. Additionally, the composition may further include additional ingredients that are commonly used in food compositions to improve an odor, taste, visual appearance, etc. (e.g., vitamins A, C, D, E, B1, B2, B6, B12, niacin, biotin, folate, pantothenic acid, etc.). Additionally, the composition may also include minerals (e.g., Zn, Fe, Ca, Cr, Mg, Mn, Cu, etc.). Additionally, the composition may also include amino acids (e.g., lysine, tryptophan, cysteine, valine, etc.). Additionally, the composition may also include food additives, such as antiseptics (e.g., potassium sorbate, sodium benzoate, salicylic acid, sodium dehydroacetate, etc.), disinfecting agents (e.g., bleaching powder and high-test bleaching powder, sodium hypochlorite, etc.), antioxidants (e.g., butylhydroxyanisole (BHA), butylhydroxytoluene (BHT), etc.), colorants (e.g., tar dye, etc.), color fixing agents (e.g., sodium nitrite, sodium nitrite etc.), bleaching agents (e.g., sodium sulfite), seasoning agents (e.g., MSG, sodium glutamate, etc.), sweeteners (e.g., dulcin, cyclamate, sodium saccharin, etc.), fragrances (e.g., vanillin, lactones, etc.), blowing agents (e.g., alum, potassium D-bitartrate, etc.), fortifying agents, emulsifying agents, thickening agents, adhesive pastes, gum bases, antifoaming agents, solvents, and improving agents. The additives may be selected according to the type of food and may be used in suitable amounts.

Meanwhile, a health functional food composition for ameliorating the symptoms of a retinal diseases may be prepared using a food composition containing the maple leaf extract or fraction thereof.

In a specific embodiment, processed foods that can ameliorating the symptoms of a retinal diseases may be prepared using the food composition. For example, a health functional food may be prepared in the form of confectionery, beverages, alcohol, fermented foods, canned foods, processed dairy foods, processed meat foods, or processed noodle foods. In particular, the confectionery may include biscuits, pies, cakes, breads, candies, jellies, gums, cereals (meal substitutes such as grain flakes, etc.), etc. Examples of the beverages may include drinking water, carbonated drinks, functional ion drinks, juices (e.g., apple, pear, grape, aloe, tangerine, peach, carrot, tomato juices, etc.), sweet rice drinks, etc. Examples of the alcohol may include refined rice wine, whiskey, soju, beer, liquor, fruit wine, etc. Examples of the fermented foods may include soy sauce, soybean paste, red pepper paste, etc. Examples of the canned foods may include canned marine products (e.g., canned products of tuna, mackerel, pacific saury, conch, etc.), canned meat products (canned products of beef, pork, chicken, turkey, etc.), canned agricultural products (canned products of corn, peach, pineapple, etc.), etc. Examples of the processed dairy foods may include cheese, butter, yogurt, etc. Examples of the processed meat foods may include pork cutlet, beef cutlet, chicken cutlet, sausage, sweet-and-sour pork, nuggets, Neobiani, etc. Noodles such as sealing-packed wet noodles may be included. Additionally, the food composition may be used in retort foods, soups, etc.

As used herein, the term "health functional food", i.e., food for special health use (FoSHU), refers to a food with high medicinal and medical effects so as to efficiently exhibit a bioregulatory function in addition to a function of nutrient supply. The health functional food may be prepared in various forms (e.g., tablets, capsules, powders, granules, liquids, pills, etc.) to obtain useful effects for ameliorating the symptoms of a retinal diseases.

To achieve the above objects, still another aspect of the present invention provides a feed composition for ameliorating the symptoms of a retinal diseases, containing a maple leaf extract or fraction thereof.

The feed composition can prevent or ameliorating the symptoms of a retinal diseases by including a maple leaf extract or fraction thereof in a feed for a subject suspected of having a retinal disease and feeding it the same.

DETAILED DESCRIPTION OF THE INVENTION

Hereinafter, the present invention will be described in more detail with reference to the following Examples. However, these Examples are for illustrative purposes only, and the scope of the invention is not limited by these Examples.

Example 1: Oral or Ocular Administration

Example 1-1: Experimental Animals and Method of Treatment

Balb/c mice (6 weeks old) were used as experimental animals. The experimental animals of Group 1 were treated with N-ethyl-N-nitrosourea (ENU; 600 mg/kg) of Formula 1 below, and the experimental animals of Group 2 were treated an ethanol maple extract and a hot water maple extract in addition to the ENU, and their protective action against retinal diseases was confirmed.

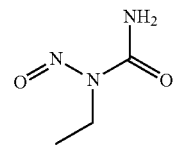

Formula 1

As shown in Table 1 below, among the maple leaf extracts, the hot water extract was orally administered at a concentration of 200 mg/kg while the ethanol extract was orally administered at concentrations of 100 mg/kg and 200 mg/kg. Further, in addition to the above administrations, the administration of the ethanol extract was also performed by direct ocular administration at a concentration of 2 mg/kg (5 days).

TABLE 1

| | Condition (Population) | Protein Prep. | Whole Eye |
|---|---|---|---|
| 1 | Normal (6) | 6 | 6 |
| 2 | ENU 600 mg/kg (6) | 6 | 6 |
| 3 | ENU 600 mg/kg + KIOM-2015EE 100 mg/kg (6) - P.O. | 6 | 6 |
| 4 | ENU 600 mg/kg + KIOM-2015EE 200 mg/kg (6) - P.O. | 6 | 6 |
| 5 | KIOM-2015EE 100 mg/kg (6) - P.O. | 6 | 6 |
| 6 | KIOM-2015EE 200 mg/kg (6) - P.O. | 6 | 6 |
| 7 | ENU 600 mg/kg + KIOM-2015EW 200 mg/kg (6)-P.O. | 6 | 6 |
| 8 | KIOM-2015EW 200 mg/kg (6) - P.O. | 6 | 6 |
| 9 | ENU 600 mg/kg + KIOM-2015EE 2 mg/kg (6)-E.D. | 6 | 6 |
| 10 | KIOM-2015EE 2 mg/kg (6) - E.D. | 6 | 6 |

(KIOM-2015EW: water extract, KIOM-2015EE: 25% EtOH, E.D.: topical eye drop, P.O.: oral administration)
(Eye drop administration was performed 3 times daily: at 9:00 AM, 1:00 PM, and 5:00 PM, and oral administration was performed once daily at 3:00 PM.)

Example 1-2: Immunohistochemical Staining Method

Tissues were fixed in 10% neutral formalin and the paraffin-embedded tissues were successively sectioned at 4

μm intervals, and one tissue slice was stained with Hematoxylin-Eosin (H&E) and the remaining tissue slices were attached to slides for immunohistochemical staining. The tissue slices were treated with $H_2O_2$ for 30 minutes to remove endogenous peroxidase. The anti-PKCalpha, anti-GFAP, and anti-GFAP antibody were each diluted at a 1:50 ratio, cultured overnight at 4° C., and washed, and were then labeled with a secondary antibody and observed under a microscope.

Experimental Results of Immunohistochemical Staining Method

Each extract stained with H&E did not show any toxicity. In the group administered with ENU, it was confirmed that the thickness of the retina of the experimental animals was thinned and the regions of the outer nuclear layer and the layer of rods and cones were lost. However, in the group administered with the ethanol maple extract at a concentration of 200 mg/kg, the thickness of the retina of the experimental animals was maintained at a level histologically similar to that of the control group (FIG. 1).

Figure 2:
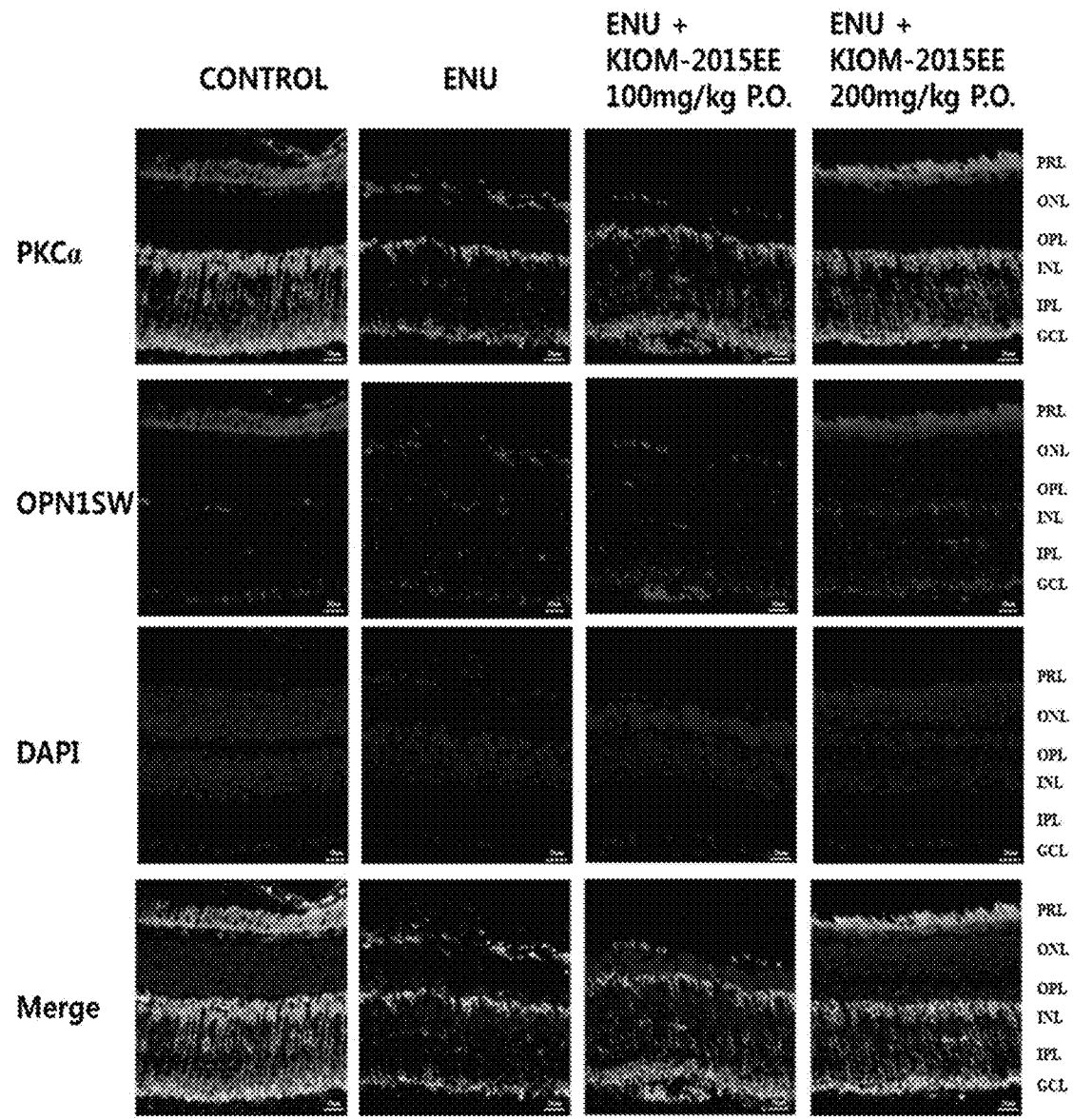
FIG. 2 shows images illustrating the results of immunohistochemical staining observed after oral or ocular administration of a maple leaf extract according to the present invention, in which the retinal protection exhibited by the ethanol maple extract when stained with OPNISW was confirmed.

Additionally, when each extract was stained using the OPN1SW (i.e., a photoreceptor cell antibody) via the immunohistochemical staining method, it was confirmed that the retinas of the experimental animals were protected in the group where the ethanol maple leaf extract was administered at a concentration of 200 mg/kg, whereas such protection was not shown in the group administered with ENU. Additionally, when each extract was stained with the PKCalpha (i.e., an index for bipolar cells), it was confirmed that the administration of the ethanol maple extract protected cell bodies and axons from being damaged (FIG. 2).

Figure 3:
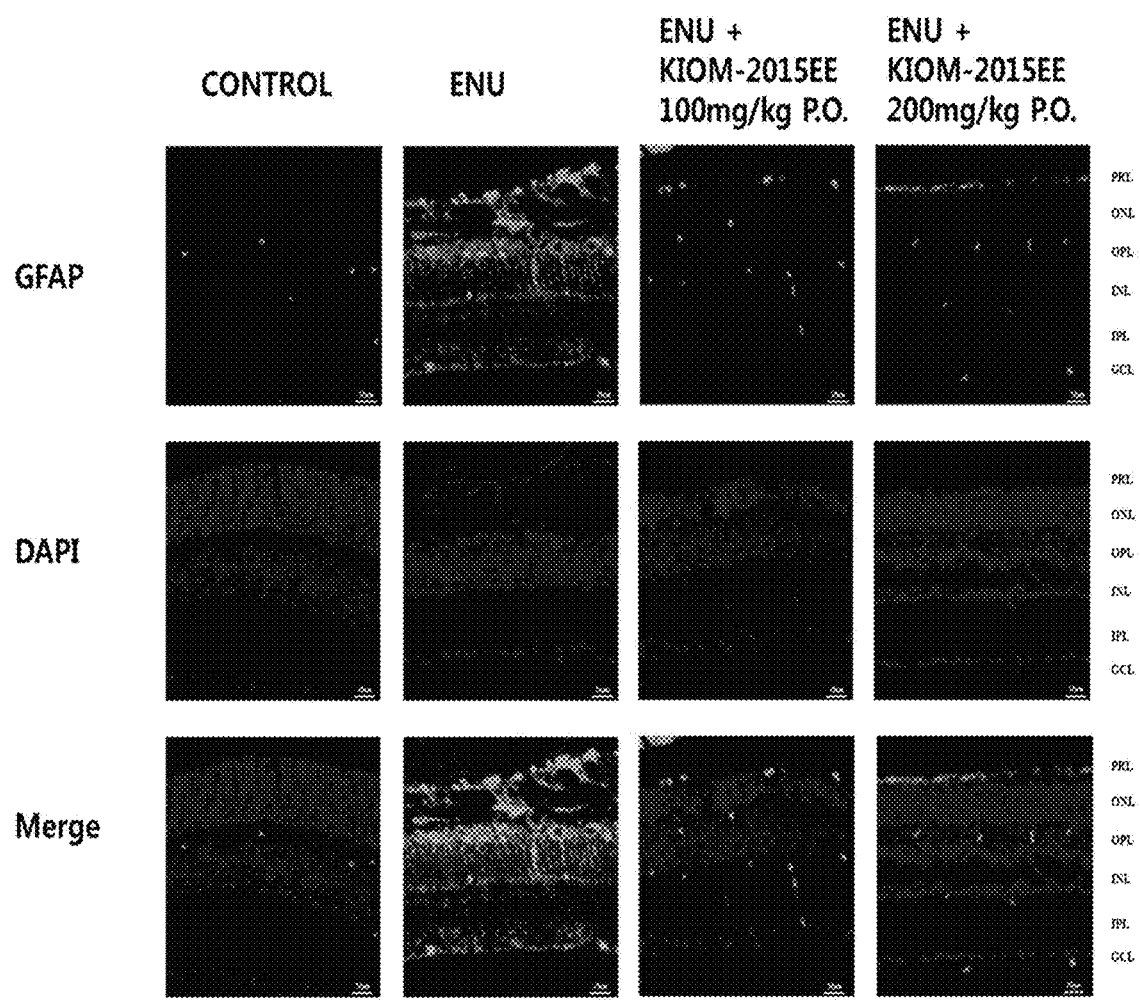
FIG. 3 shows images illustrating the results of immunohistochemical staining observed after oral or ocular administration of a maple leaf extract according to the present invention, in which the decrease of the GFAP expression level in groups treated with the ethanol maple extract when stained with GFAP was confirmed.

Additionally, when each extract was stained using the GFAP (i.e., an index protein for Muller cells), it was confirmed that the level of GFAP expression was reduced in the group where the ethanol maple extract was treated at a concentration of 200 mg/kg (FIG. 3).

Example 1-3: TUNEL Assay

The analysis was performed via an in situ method using the terminal deoxynucleotidyl transferase (TdT)-dUTP nick end labeling assay kit (Roche Diagnostic, Mannheim, Germany).

The tissues used in the immunohistochemical staining method were deparaffinized and reacted in a TUNEL reaction mixture (terminal deoxynucleotidyl transferase (TdT)-dUTP) for 1 hour at 37° C. in a darkroom and observed by fluorescence microscopy (515 nm to 565 nm, green, Olympus optical, Tokyo, Japan).

Experimental Results of TUNEL Assay

Figure 4:
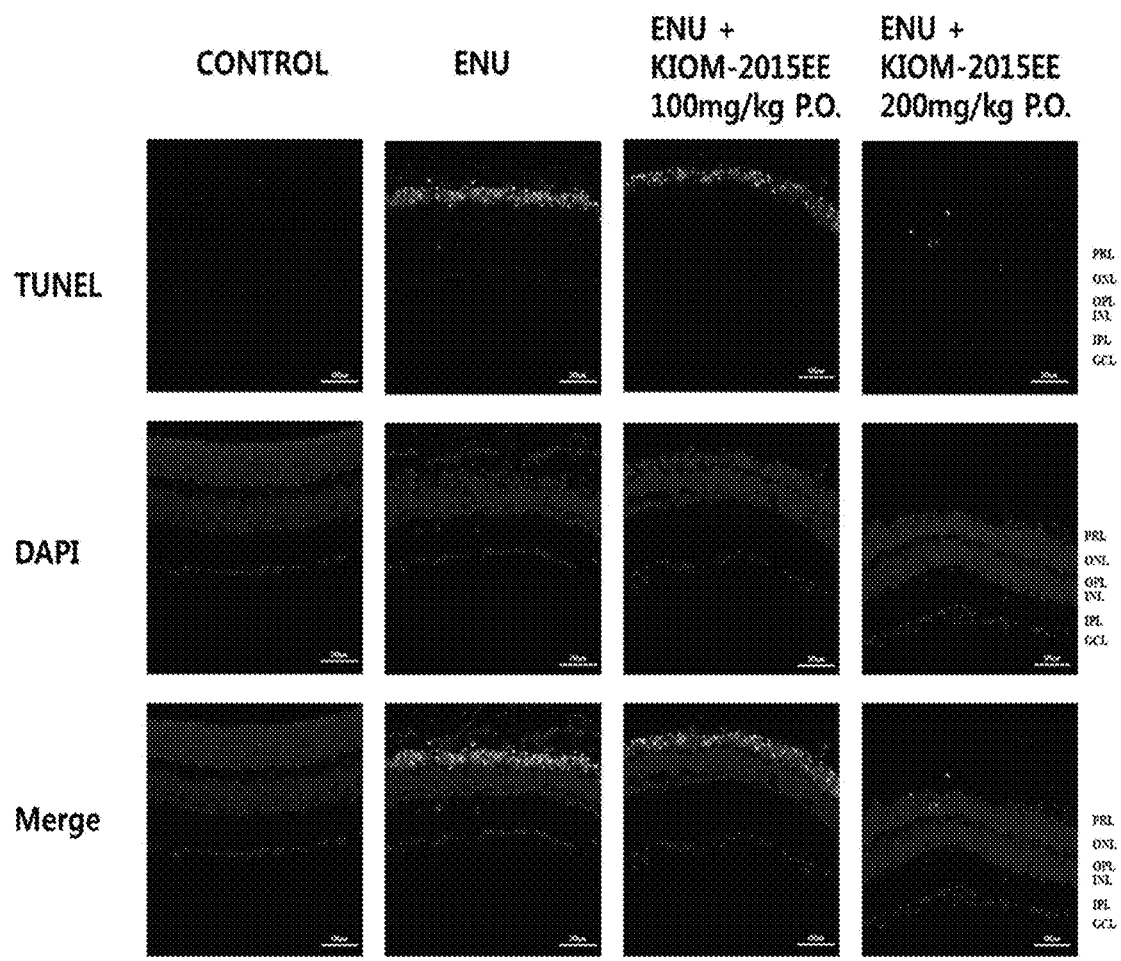
FIG. 4 shows fluorescence microscopic images illustrating the results of a TUNEL assay after oral or ocular administration of a maple leaf extract according to the present invention.

Upon confirmation of cell death by the TUNEL assay, it was confirmed that the ethanol maple leaf extract at a concentration of 200 mg/kg inhibited the cell death (FIG. 4).

Example 1-4: Western Blot

Each retina was extracted from the eyeball, and the proteins therein were extracted with RIPA buffer and precipitated by centrifugation at 12,000 rpm for about 10 minutes, and thereby a supernatant was obtained. The proteins in the supernatant were quantified by the Bradford (Bio-Rad, Hercules, Calif., U.S.A.), electrophoresed on 7% to 12% SDS PAGE, and transferred onto a nitrocellulose membrane. The nitrocellulose membrane was first treated with each antibody, reacted with a secondary antibody to which peroxidase was conjugated, and analyzed by performing enhanced chemiluminescence (ECL, Amersham Biosciences, England).

Experimental Results of Western Blot

Figure 5:
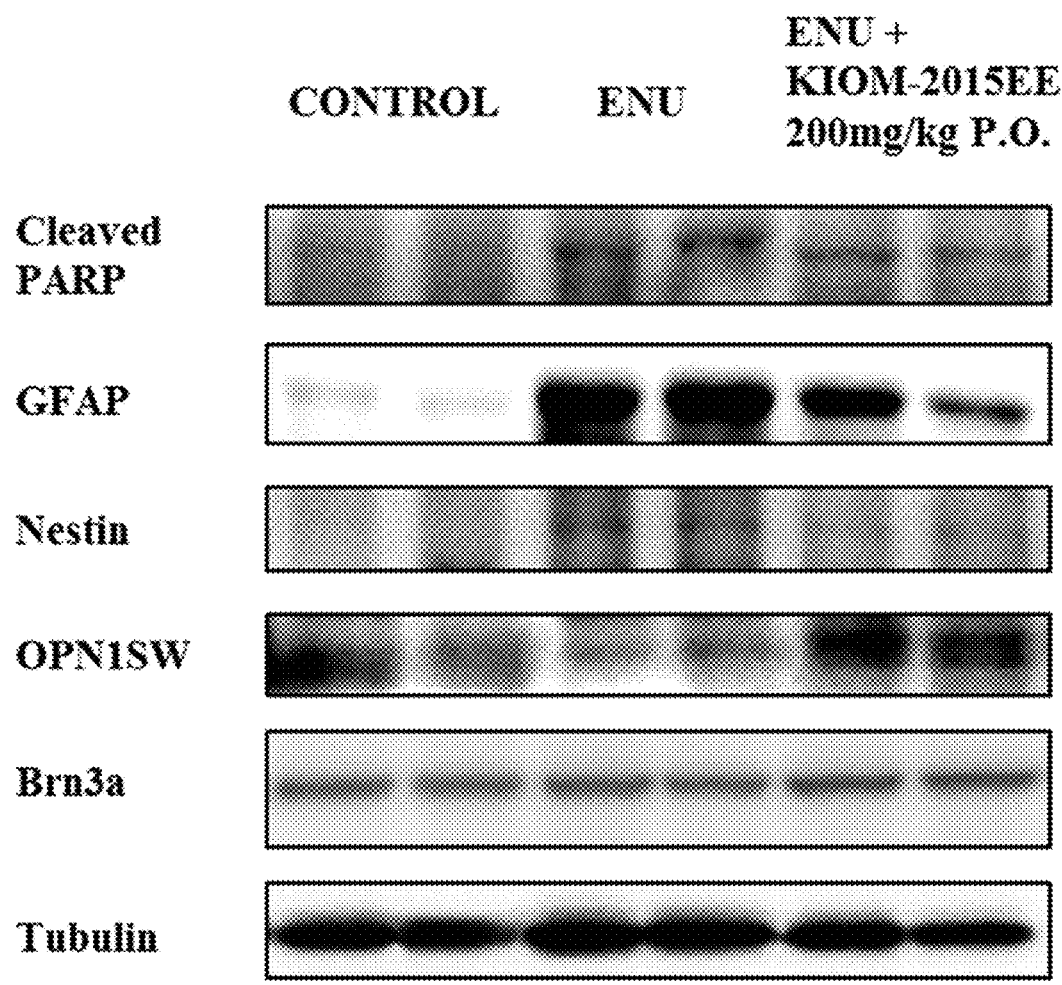
FIG. 5 shows images illustrating the results of a western blot analysis after oral or ocular administration of a maple leaf extract.

The levels of protein expression were examined by western blot. As a result, it was confirmed that in a case where the ethanol maple extract was administered ($5^{th}$ and $6^{th}$ lanes from left: 200 mg/kg), the expression levels of Cleaved PARP, GFAP, and Nestin were reduced. In contrast, it was confirmed that the expression level of the OPN1SW was significantly increased compared to the group where ENU was treated (FIG. 5).

Example 2: Eye Drop or Oral Administration

Example 2-1: Method of fMCAO Surgery

During the surgery, each white rat model of ischemic stroke caused by middle cerebral artery occlusion (MCAO) was maintained to have a body temperature of 37.0±0.5° C. while being kept under anesthesia. The skin on the central part of the anterior neck of the anesthetized rat was excised, and the muscle layer of the neck was exposed. Then, the left common carotid artery was located and carefully separated/dissected so as not to damage the vagus nerve. After fixing the common carotid artery, the branches of the external carotid artery and internal carotid artery were carefully separated and the external carotid artery was blocked. Then, while temporarily blocking the blood flow of the common carotid artery, part of the common carotid artery was excised and nylon suture thread was inserted thereinto so as to block the middle cerebral artery. After 90 minutes, the suture thread was carefully removed to restart the flow of blood and an animal model was induced therefrom.

Example 2-2: Conditions and Plans for Experiments

TABLE 2

| | Condition (Population) | 5 D Harvested | Flat Mount | Whole Eye |
|---|---|---|---|---|
| 1 | Normal (3) | ○ | 5 | 6 |
| 2 | fMCAO + Sham (3) | ○ | 5 | 6 |
| 3 | fMCAO + Vehicle (PBS) (11) - E.D. | ○ | 5 | 6 |
| 4 | fMCAO + KIOM-2015EW 2 mg/mL (11) - E.D. | ○ | 5 | 6 |
| 5 | fMCAO + KIOM-2015EE 1 mg/mL (11) - E.D. | ○ | 5 | 6 |
| 6 | fMCAO + KIOM-2015EE 2 mg/mL (11) - E.D. | ○ | 5 | 6 |

TABLE 2-continued

| | Condition (Population) | 5 D Harvested | Flat Mount | Whole Eye |
|---|---|---|---|---|
| 7 | fMCAO + KIOM-2015EE 100 mg/kg (11) - P.O. | ○ | 5 | 6 |
| 8 | fMCAO + KIOM-2015EE 200 mg/kg (11) - P.O. | ○ | 5 | 6 |
| 9 | fMCAO + Ginexin-F 20 mg/kg (11) - P.O. | ○ | 5 | 6 |
| | Immunofluorescence/H&E Staining | | Brn3a/Tuj-1/GFAP | Paraffin Embedding |

(KIOM-2015EW: water extract, KIOM-2015EE: 25% EtOH, E.D.: topical eye drop, P.O.: oral administration)
(Eye drop administration was performed 3 times daily: at 9:00 A.M., 1:00 P.M., and 5:00 P.M., and oral administration was performed once daily at 3:00 P.M.)

Table 2 above (KIOM-2015EW: water maple leaf extract, KIOM-2015EE: 25% ethanol maple extract, E.D.: topical eye drop, P.O.: oral administration) shows drug administration patterns according to experimental conditions.

Meanwhile, eye drop administration was performed 3 times daily at 9:00 A.M., 1:00 P.M., and 5:00 P.M., and oral administration was performed once daily at 3:00 P.M. The eyes of the experimental animals were exposed to the drugs for a total of 5 days and sacrificed on the 5$^{th}$ day after the last administration.

Genexin-F Tab. of SK Chemicals, which is prescribed to patients with ischemic retinopathy, was used as a positive control agent suitable for a model with optic nerve cell damage due to ischemia, and the dose was administered after calculation based on the amount of food eaten once daily relative to body weight (6 mg/mL based on rat (300 g)).

Example 2-3: Experimental Results of Example 2

Experimental Results Confirming Inhibition of Cell Death of Retinal Ganglion Cells by KIOM-2015E in Animal Model with Ischemic Retinal Nerve Degeneration (KIOM-2015EE-Mediated Protection of RGC Degradation After fMCAO-Induced Ischemic Damage)

The eyeballs of the rats which were sacrificed on the 5$^{th}$ day were extracted and fixed in 4% PFA for 10 minutes. Then, only retinal tissues were isolated under a dissecting microscope and each retina tissue was cut at four edges and flattened, and fixed and stored in MeOH for use. The MeOH was removed for staining, and the retinal tissues were washed twice in TBS for 5 minutes. Then, to promote smooth penetration of antibodies through the cell membrane while preventing non-specific binding of the antibodies, the retinal tissues were reacted with 0.3% Triton X-100+0.2% BSA+5% normal goat serum/TBS at room temperature for 60 minutes. Subsequently, the primary antibody, Brn3a (i.e., a ganglion cell marker), was allowed to react at room temperature for 1 hour and then removed, and then further reacted with Alexa Fluor 488 goat anti-mouse IgG (i.e., a secondary antibody) at room temperature for 1 hour. The resulting retinal tissues were subjected to nuclear staining with DAPI for 10 minutes and imaged upon observation by fluorescence microscopy.

Figure 6A:
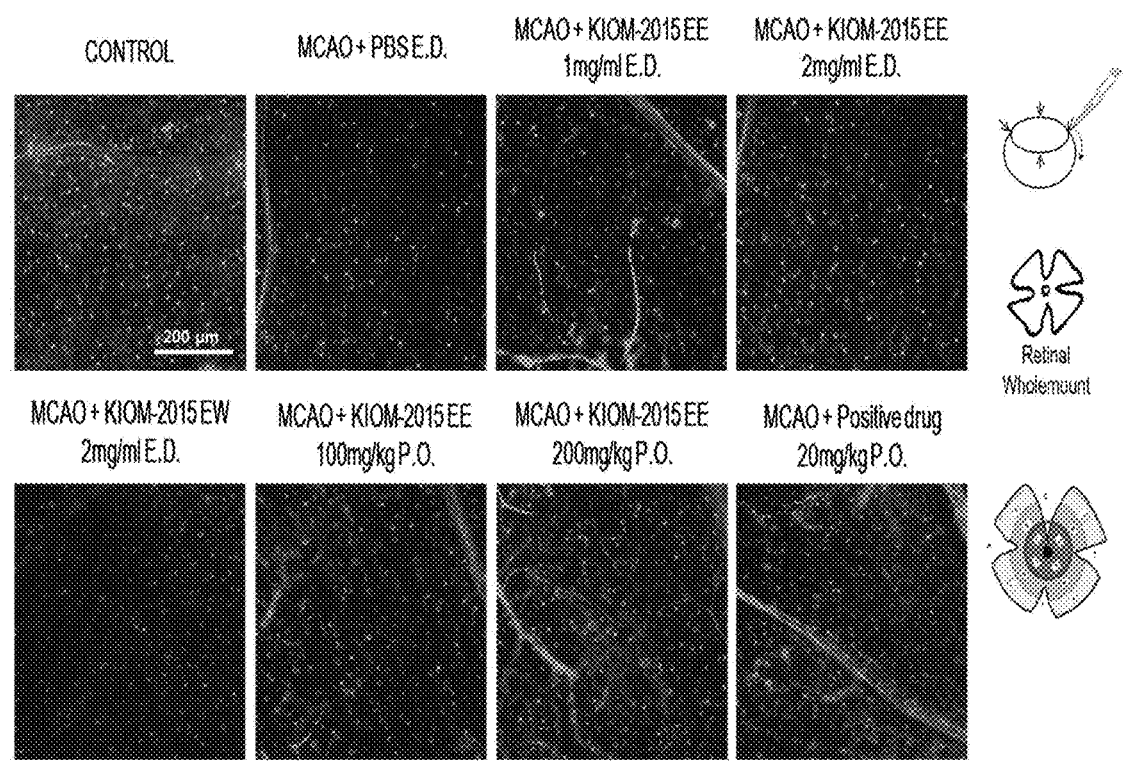
Figure 6B:
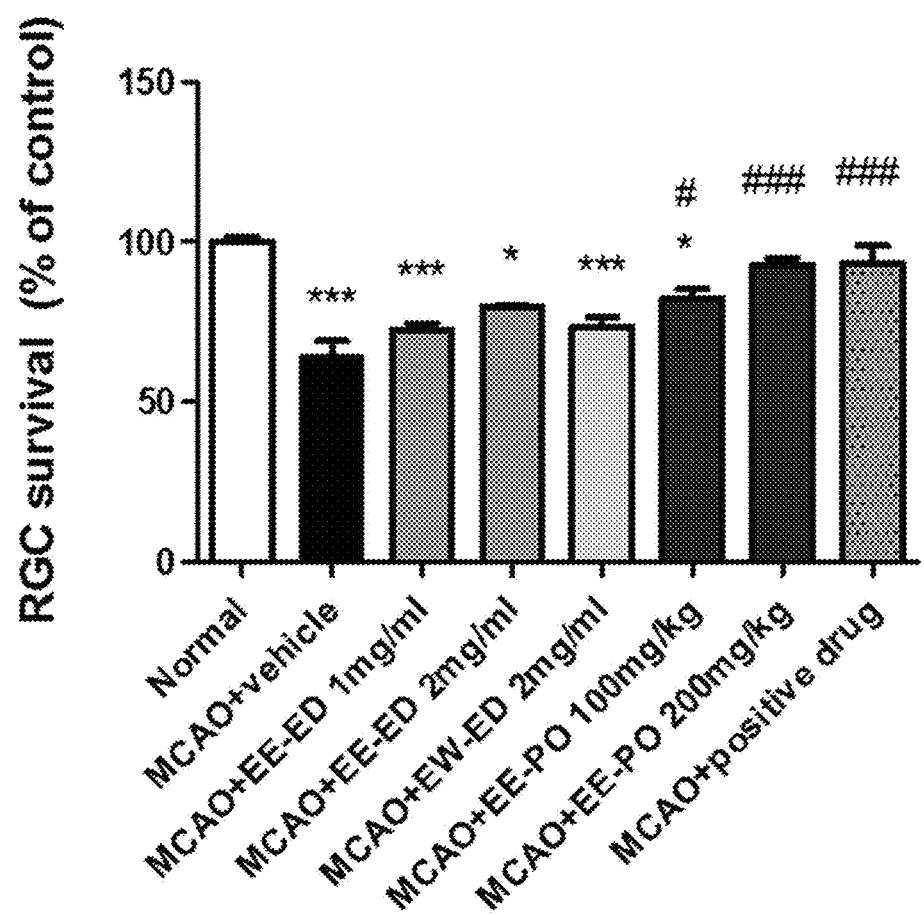

FIGS. 6a-b show the results obtained therefrom. Specifically, FIG. 6a shows images obtained by reacting Brn3a (i.e., a specific antibody of retinal ganglion cells (RGCs)) among the retinal tissue-constituting cells; and FIG. 6b shows a graph illustrating the results where five images were randomly selected from the images and the number of cells showing a positive reaction to Brn3a in each selected image was calculated and then converted to an average value (%) for the control group. It was confirmed from FIG. 6b that the ethanol maple extract can inhibit the cell death of ganglion cells better than the water maple extract, and that the ethanol maple extract showed results similar to the positive control group. The images were taken at 100× magnification.

Experiments Confirming Inhibition of Decrease in Retinal Ganglion Cell Fibers by KIOM-2015E in Animal Model with Ischemic Retinal Nerve Degeneration (KIOM-2015E-Mediated Blockade of RGC Nerve Fiber Degradation After fMCAO-Induced Ischemic Damage)

Figure 7A:
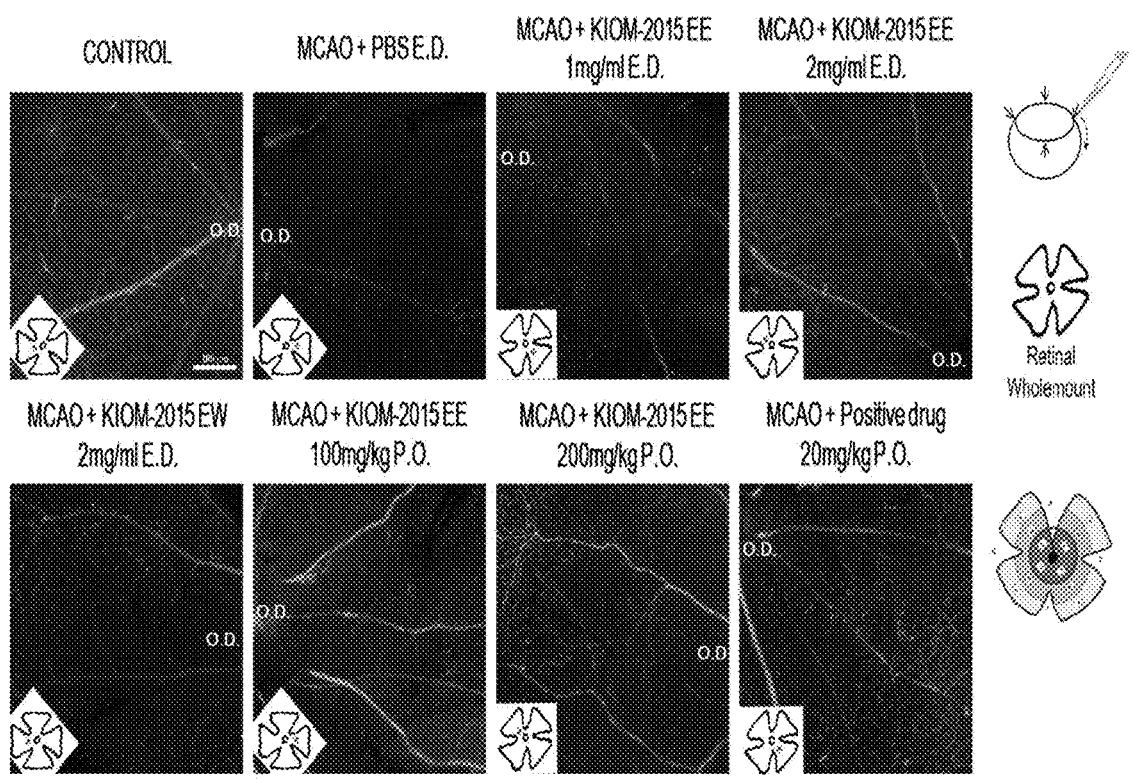

Immunofluorescence staining was performed in the same manner as in Experimental Example 2-1. FIG. 7a shows images illustrating the results of fluorescence staining using neuron-specific Class III β-tubulin (Tuj-1) antibody, which is a marker for neurons and nerve fibers. The nerve fibers were observed by fluorescence microscopy and imaged.

Figure 7B:
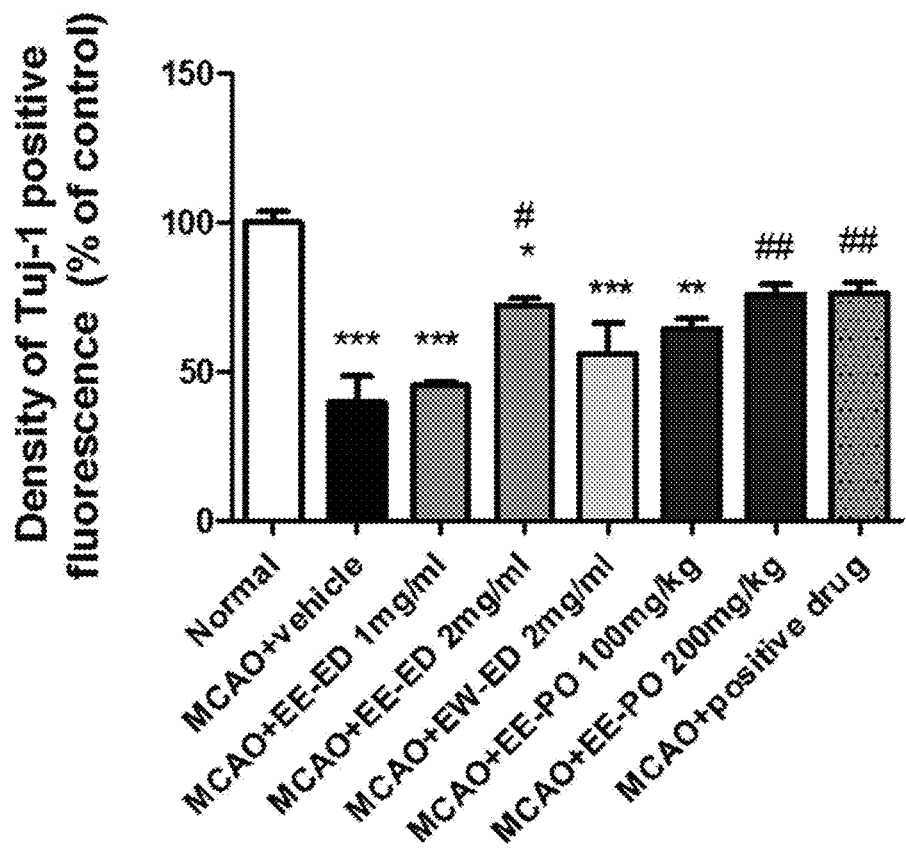

In FIG. 7b, the expression of the nerve fibers that showed a Tuj-1-positive response decreased by 50% or more on the 5$^{th}$ day of the MCAO surgery. However, it was confirmed that the eye drop administration at a concentration of 2 mg/mL was more effective than at a concentration of 1 mg/mL, and the eye drop administration of KIOM-2015EE (2 mg/mL) was more effective than KIOM-2015EW (2 mg/mL). Additionally, it was confirmed that oral administration was more effective in RGC nerve fiber degradation than eye drop administration. FIG. 7b shows a graph illustrating the results where five images were randomly selected from the images and the fluorescence density showing a positive reaction to Tuj-1 was obtained in terms of pixel values using the ImageJ program and expressed as an average value (%) for the control group. The images were taken at 100× magnification.

Experiments Confirming Inhibition of Activities of Neuroglial Cells and Astrocytes by KIOM-2015E in Animal Model with Ischemic Retinal Nerve Degeneration (KIOM-2015E-Mediated Blockade of Astrocyte Activation after fMCAO-Induced Ischemic Damage)

Figure 8A:
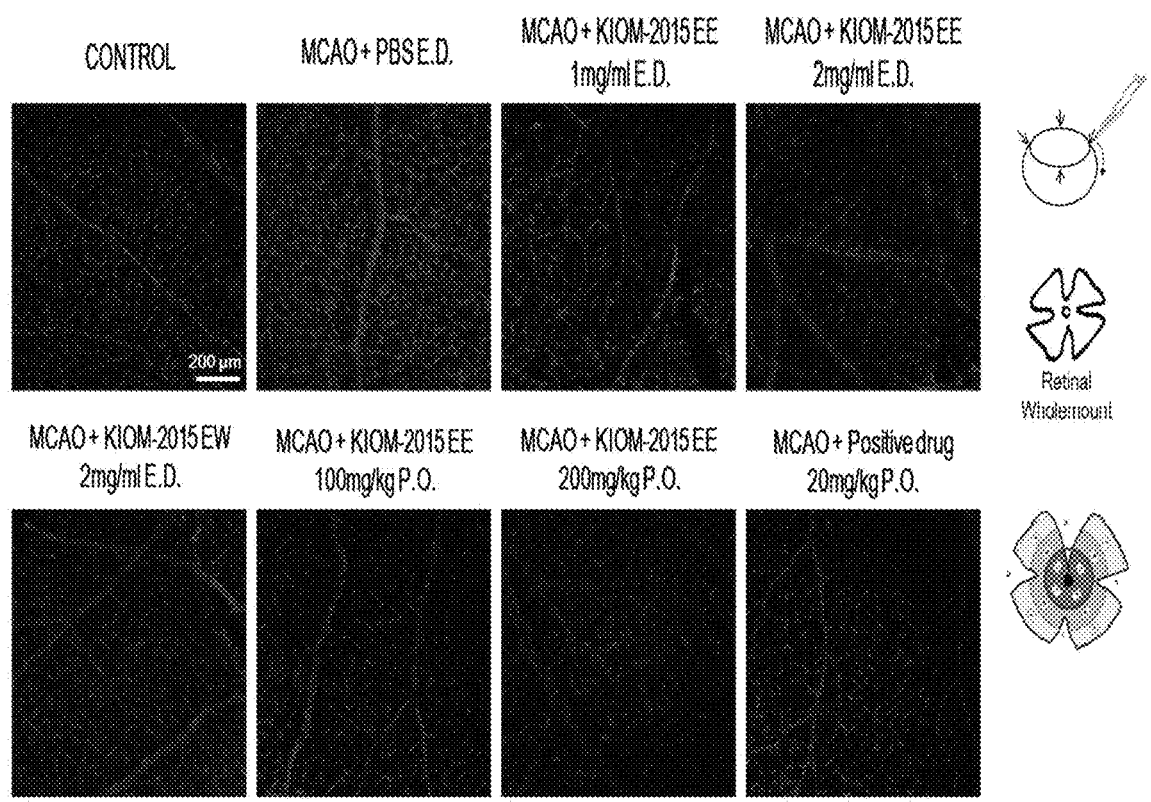

Immunofluorescence staining was performed in the same manner as in Experimental Example 2-1. FIG. 8a shows images illustrating the results of fluorescence staining using glial fibrillary acidic protein (GFAP) antibody, which is a marker for neuroglial cells and astrocytes. The astrocytes were observed by fluorescence microscopy and imaged.

Figure 8B:
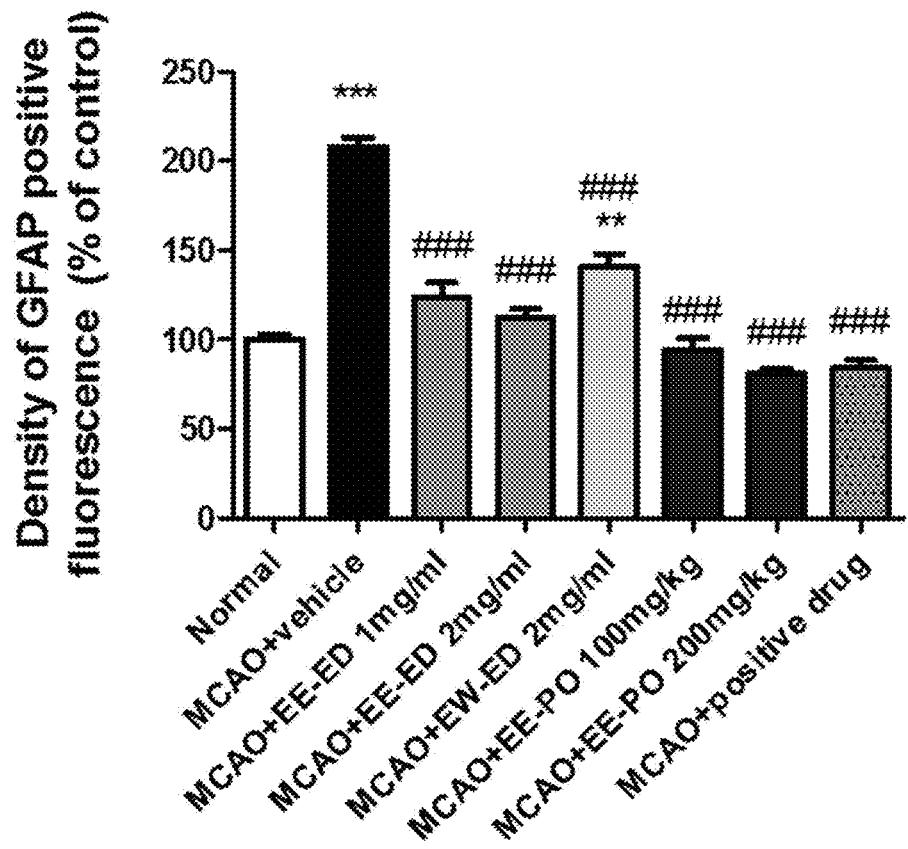

Astrocytes and neuroglial cells are among the glial cells that are activated around the damaged regions. These cells are frequently activated when damage occurs in tissues, and the increase/decrease in the level of GFAP (i.e., a marker for astrocytes) was confirmed. On the 5$^{th}$ day after the MCAO surgery, it was confirmed that the level of GFAP expression was significantly increased, and it was also confirmed from FIG. 8b that expression levels were significantly decreased by KIOM-2015E. FIG. 8b shows a graph illustrating the results where five images were randomly selected from the images and the fluorescence density showing a positive reaction to GFAP was obtained in terms of pixel values using the ImageJ program and expressed as an average value (%) for the control group. The images were taken at 100× magnification.

Experiments Confirming Changes in Retinal Histology by KIOM-2015E in Animal Model with Ischemic Retinal Nerve Degeneration (Representative Photomicrographs of Hematoxylin and Eosin Stained Retinal Sections)

To confirm the histological changes of the retina, the collected eyeballs were fixed in a 4% PFA solution, and finally the paraffin was infiltrated to embed the tissues and cut into a thickness of 3 μm using a microtome. After removing paraffin in a drying oven for 1 hour and subsequent hydration, the tissues were stained with a hematoxylin and eosin solution for 5 minutes, washed, and mounted, and the morphological and histological changes in the retina were examined by microscopy.

Figure 9A:
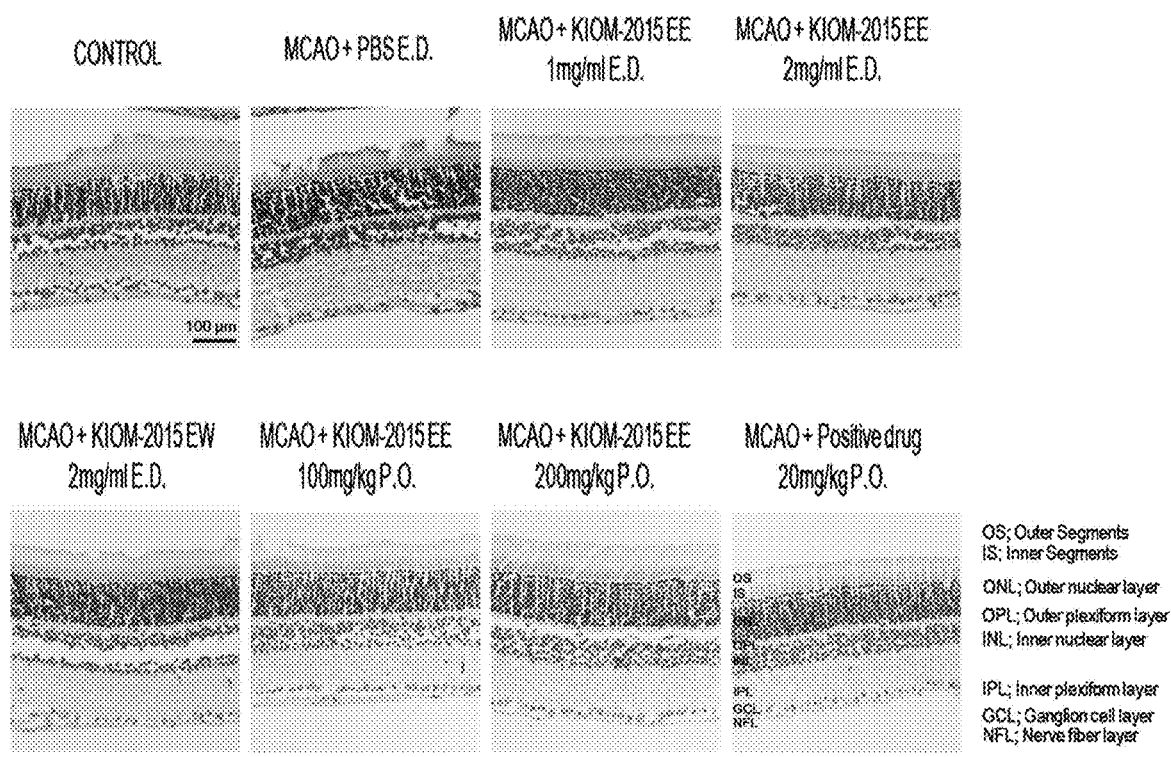
Figure 9B:
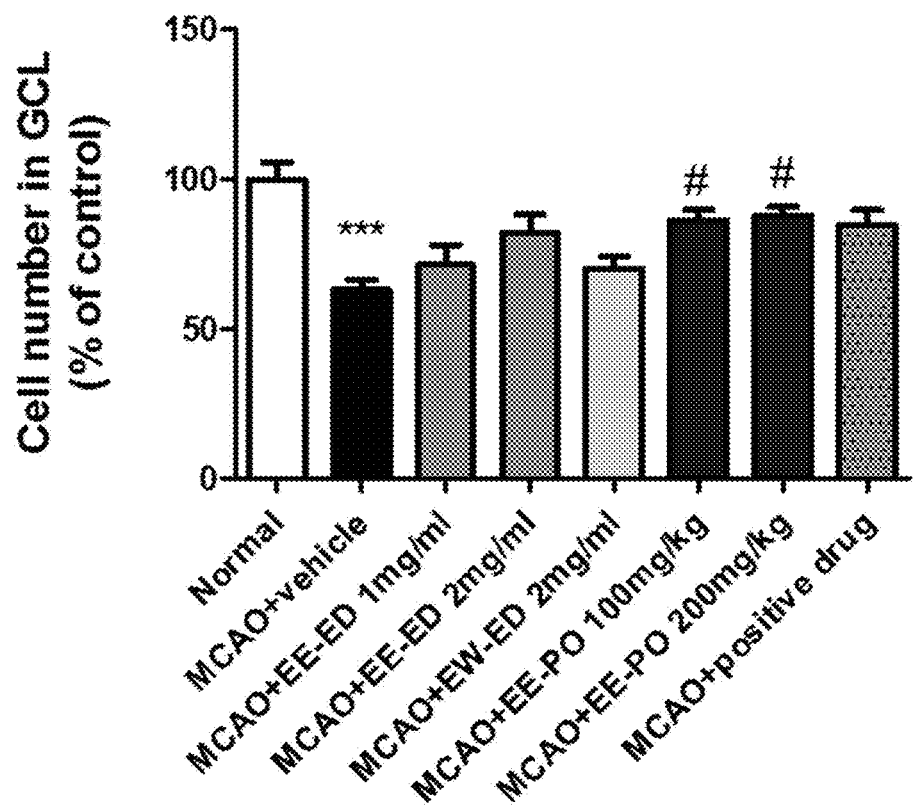

It was observed from FIG. 9a that on the 5$^{th}$ day after the MCAO surgery, the thickness of the retinal tissue increased due to the swelling of the inner plexiform layer (IPL), and the number of cells in the ganglion cell layer (GCL) decreased significantly. Additionally, it was confirmed that the structures of the photoreceptor cell layer and the outer segment were dislodged or irregular. However, it was observed that this change was inhibited in all of the groups including eye drop administration and oral administration of KIOM-2015E (FIG. 9b). FIG. 9b shows a graph illustrating the results where five images were randomly selected from the images and the number of cells remaining in the ganglion cell layer was counted and expressed as an average value (%) for the control group. The images were taken at 100× magnification.

Experiments Confirming Inhibition of Cell Death of Retinal Tissue by KIOM-2015E in Animal Model with Ischemic Retinal Nerve Degeneration (Representative Images of Retinas After TUNEL Assay and Counterstaining with DAPI)

The TUNEL assay (Roche Diagnostics, Cat. No. 11 684 795 910) was performed according to the manual so as to confirm the effects of KIOM-2015E on cytotoxicity and cell death induced by MCAO surgery, and the images of TUNEL-positive cells were obtained by fluorescence microscopy.

Figure 10:
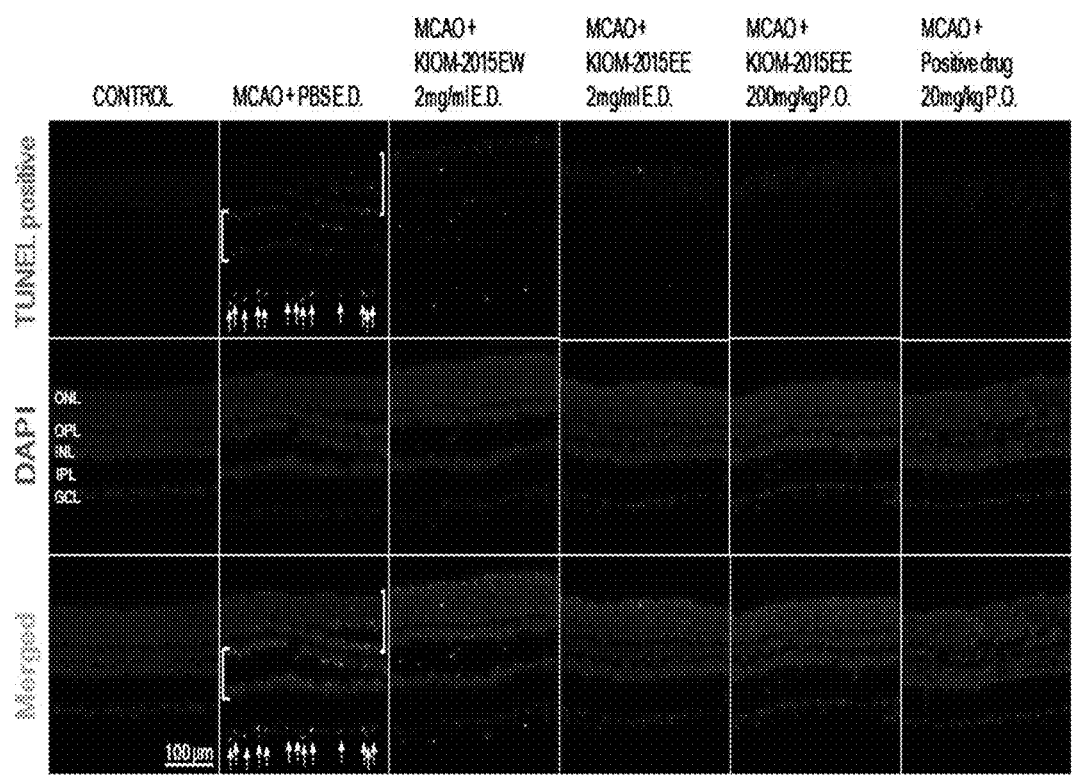
FIG. 10 shows fluorescence microscopic images illustrating the experimental results confirming the inhibition of cell death of retinal tissue after eye drop or oral administration of a maple leaf extract according to the present invention.

It was observed from FIG. 10 that on the 5$^{th}$ day after the MCAO surgery, the TUNEL-positive response was also observed the inner nuclear layer and the outer nuclear layer, in addition to the ganglion cell layer. Additionally, it was confirmed that the number of cells showing a TUNEL-positive response was decreased in all of the administration groups including the eye drop and oral administration of KIOM-2015E. The images were taken at 100× magnification.

From the foregoing, it was confirmed that a maple leaf extract can increase the expression level of OPNISW, Brn3a, and Tuj-1 while preventing damage to the retina and decreasing the expression level of proteins that cause retinal diseases, and it was confirmed that retinal diseases can be prevented or treated using the pharmaceutical composition according to the present invention.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for treating a retinal disease, comprising a step of administering a pharmaceutically effective amount of a composition which comprises a maple leaf extract to a subject in need thereof, wherein the retinal disease comprises nerve damage or ischemic damage to the retina or macula thereof or degeneration therefrom, and wherein the retinal disease is at least one disease selected from the group consisting of retinal artery occlusion, retinal vein occlusion, retinal periphlebitis, hypertensive retinopathy, diabetic retinopathy, retinopathy of prematurity, sensory neuroretinal inflammation, inflammation of the retinal pigment epithelium, retinitis pigmentosa, angioid streaks, drusen, rhegmatogenous retinal detachment, non-rhegmatogenous retinal detachment, macular degeneration, macular dystrophy, diabetic retinopathy, retinal arteriovenous occlusion, hypertensive retinopathy, retinal aortic aneurysm, retinal ischemic syndrome, radiation retinopathy, retinopathy of prematurity, acute retinal necrosis, retinitis, retinal choroiditis, retinal detachment, retinal tumor, retinal damage due to trauma, and retinal damage due to light.

2. The method of claim 1, wherein the pharmaceutical composition reduces the expression of at least one selected from the group consisting of Cleaved PARP, GFAP, and Nestin.

3. The method of claim 1, wherein the pharmaceutical composition increases the expression of at least one selected from the group consisting of OPNISW, Brn3a, and Tuj-1.

* * * * *